United States Patent
Fan et al.

(10) Patent No.: US 10,766,895 B2
(45) Date of Patent: Sep. 8, 2020

(54) PREPARATION METHODS FOR PALBOCICLIB FREE BASE CRYSTAL FORM A AND CRYSTAL FORM B

(71) Applicants: Zhejiang Huahai Pharmaceutical Co., Ltd., Linhai (CN); Shanghai Syncores Technologies Inc. Ltd., Shanghai (CN)

(72) Inventors: Haisheng Fan, Shanghai (CN); Xiaowen Guo, Shanghai (CN); Luning Huang, Shanghai (CN); Hong Gu, Shanghai (CN)

(73) Assignees: ZHEJIANG HUAHAI PHARMACEUTICAL CO., LTD., Linhai (CN); SHANGHAI SYNCORES TECHNOLOGIES INC. LTD., Shanghai (CN)

( * ) Notice: Subject to any disclaimer, the term of this patent is extended or adjusted under 35 U.S.C. 154(b) by 0 days.

(21) Appl. No.: 16/405,722

(22) Filed: May 7, 2019

(65) Prior Publication Data

US 2019/0263809 A1   Aug. 29, 2019

Related U.S. Application Data

(62) Division of application No. 15/772,497, filed as application No. PCT/CN2016/104330 on Nov. 11, 2016, now Pat. No. 10,329,290.

(30) Foreign Application Priority Data

Nov. 2, 2015 (CN) .......................... 2015 1 0733519

(51) Int. Cl.
  *C07D 487/04* (2006.01)
  *C07D 471/04* (2006.01)
  *B01D 9/00* (2006.01)
  *A61K 31/519* (2006.01)

(52) U.S. Cl.
  CPC ......... *C07D 471/04* (2013.01); *B01D 9/0054* (2013.01); *B01D 9/0063* (2013.01); *A61K 31/519* (2013.01)

(58) Field of Classification Search
  CPC .................................................... C07D 487/04
  USPC ......................................................... 544/279
  See application file for complete search history.

(56) References Cited

U.S. PATENT DOCUMENTS 7,781,583 B2   8/2010   Erdman et al.

FOREIGN PATENT DOCUMENTS

| CN | 101001857 A | 7/2007 |
| CN | 105008357 A | 10/2015 |
| CN | 105085517 A | 11/2015 |
| WO | WO2006/018341 A1 | 2/2006 |
| WO | WO2014128588 | 8/2014 |
| WO | WO 2016024249 A1 | 2/2016 |

OTHER PUBLICATIONS

International Search Report of International Application No. PCT/CN2016/104330, filed Nov. 2, 2016.
Process for the Preparation of Palbociclib Crystalline Forms, IP.Com Journal, IP.Com Inc., Jul. 2016, XP013172103, ISSN: 1533-0001.

*Primary Examiner* — Douglas M Willis
(74) *Attorney, Agent, or Firm* — Blank Rome LLP

(57) ABSTRACT

Disclosed is a preparation method for a Palbociclib free base crystal form A as shown in Formula I, comprising the following steps: treating a Palbociclib free base and/or a Palbociclib salt compound by using an inorganic base in a water solvent at the temperature of 35 to 100'C. to obtain a Palbociclib free base crystal form A, the water solvent being water or mixed solvent obtained by water and an organic solvent capable of being mixed and disclosed in the water. Also disclosed is a preparation method for a Palbociclib free base crystal form B, comprising the following steps: treating a Palbociclib salt compound by using an inorganic base in a water solvent at the temperature of 0 to 20° C. to obtain a Palbociclib free crystal form B, the water solvent being water or a mixed solvent obtained by water and an organic solvent capable of being mixed and dissolved in the water. The method is safe and convenient in operation and low in pollution, and facilitates industrial production.

9 Claims, 1 Drawing Sheet

PREPARATION METHODS FOR PALBOCICLIB FREE BASE CRYSTAL FORM A AND CRYSTAL FORM B

RELATED APPLICATIONS

This application is a divisional of U.S. Non-Provisional application Ser. No. 15/772,497, filed on Apr. 30, 2018, entitled "Preparation methods for palbociclib crystal form A and crystal form B", which is a national stage of International Patent Cooperative Treaty (PCT) Application No. PCT/CN2016/104330, filed Nov. 2, 2016, which claims the benefit of priority to Chinese Patent Application No. 201510733519.5, filed on. Nov. 2, 2015, and entitled "Preparation methods for palbociclib crystal form A and crystal form B". The entireties of the aforementioned applications are hereby incorporated in the present application by reference.

BACKGROUND OF THE INVENTION

Field of the Invention

The invention belongs to the field of chemical medicine, particularly relates to a preparation method for a crystal form A and a crystal form B of palbociclib free base.

Description of Related Art

The chemical. name of Palbociclib is 6-acetyl-8-cyclopentyl-5-methyl-2-[[5-(piperazine-1-yl) pyridine-2-yl] amino]-8H-pyrido[2,3-D]pyrimidine-7-ketone, and the structural formula thereof is shown as the formula I:

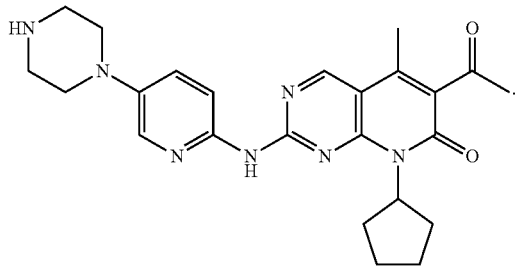

Palbociclib, developed by Pfizer, is a selective cyclin-dependent kinase (CDK) 4/6 inhibitors taken once daily, and shows a powerful therapeutic effect on postmenopausal women with positive ER and HER2 negative forms of advanced breast cancer. The drug has received FDA breakthrough therapy certification, and was approved for sale in the United State on Feb. 3, 2015.

WO2014128588A1 discloses a crystal form A and crystal form B of palbociclib free base. The crystal form A has a X-ray powder diffraction pattern comprising characteristic peaks at 2θ angels of 8.0°±0.2°, 10.1°±0.2°, 10.3°±0.2° and 11.5°±0.2°. The crystal form B has an X-ray powder diffraction pattern comprising characteristic peaks at 2θ angels of 6.0°±0.2°, 10.9°±0.2°, 12.8°±0.2°, 16.4°±0.2° and 19.8°±0.2°.

Considering that organic solvents were used in the preparation methods of both the crystal form A and the crystal form B disclosed in WO20141.28588A1, the free base form of palbociclib has a very poor solubility in all of organic solvents. For example, the required dissolution temperatures for the palbociclib free base in this patent are shown in the Table below to reach the fixed concentration of 25 mg/mL in various solvents (dissolution temperature >110° C. indicates that the palbociclib free base remains insoluble at the temperature of 110° C., that is the solubility thereof is less than 25 mg/mL):

| Experiment number | Solvent | Dissolution temperature (° C.) |
|---|---|---|
| 1 | N-butanol | >110 |
| 2 | DMF | >110 |
| 3 | NMP | 97.9 |
| 4 | DMSO | >110 |
| 5 | DMAc | >110 |
| 6 | N-butyl acetate | >110 |
| 7 | Anisole | >110 |
| 8 | 10% of n-butanol/anisole (v/v) | >110 |
| 9 | 20% of n-butanol/anisole (v/v) | 109.7 |
| 10 | 40% of n-butanol/anisole (v/v) | 101.4 |
| 11 | 10% of n-butanol/NMP (v/v) | 103.7 |
| 12 | 25% of n-butanol/NMP (v/v) | >110 |
| 13 | 10% of 1,4-butylene glycol/anisole (v/v) | 109.8 |
| 14 | 25% of 1,4-butylene glycol/anisole (v/v) | 104.8 |
| 15 | 1:1:8 propylene glycol/n-butanol/anisole (v/v) | 91.2 |
| 16 | 2:1:7 propylene glycol/butanol/anisole (v/v) | 84.1 |

Therefore, a large amount of organic solvents are required for the high-temperature extraction and liquid separation when palbociclib is free from alkali. The process has a certain of risk, creates a large number of pollution, and is difficult for the industrial production.

The present invention provides a method for obtaining crystal form A and crystal form B of palbociclib free base directly from water or a mixed solvent of water and water-miscible organic solvent. The process for industrial production is safe and convenient with less pollution.

BRIEF SUMMARY OF THE INVENTION

In order to overcome the defects of the prior arts, the present invention provides a method for preparing crystal form A and crystal form B of palbociclib free base. The method provided in the present invention can be scaled up with stable results, and is suitable for large-scale industrial production.

To achieve this object, one aspect of the present invention is to provide a method for preparing a crystal form A of palbociclib free base as shown in Formula I. The method comprises the step as follows.

A palbociclib free base and/or a palbociclib salt compound is treated with an inorganic base in an aqueous solvent at a temperature of 35° C. to 100° C. to obtain a crystal form A of palbociclib free base, wherein the aqueous solvent is water or a mixed solvent of water and water-miscible organic solvent.

In a preferred embodiment, the method comprises the following steps:

1) treating a palbociclib free base with an inorganic base in an aqueous solvent at a temperature of 35° C. to 100° C. to obtain a crystal form A of palbociclib free base; or 2) dissolving palbociclib salt compound and optionally palbociclib free base into an aqueous solvent to form a solution, and then treating the solution with an inorganic base water solvent at a temperature of 35° C. to 100° C. to obtain crystal form A of palbociclib free base, wherein the solvent is water or a mixed solvent of water and water-miscible organic solvent.

In the present invention, the palbociclib salt compounds are preferably selected from the group consisting of palbociclib isethionate, palbociclib hydrochloride, palbociclib sulfate, and palbociclib methane sulfonate, or a combinations thereof, more preferably palbociclib isethionate and/or palbociclib hydrochloride.

The palbociclib salt compound can be in solid form or solution form. It can be also a single salt or a mixture of salts or a mixture of salt and free base.

In a preferred embodiment of the present invention, the palbociclib salt compound can be formed by dissolving palbociclib free base and an acid in a solvent. The acid is selected from the group consisting of sulfuric acid, isethionic acid, methane sulfonic acid, hydrochloric acid or nitric acid.

The palbociclib free base is in a form of the palbociclib free base itself, or a crystal form B of palbociclib free base, or a mixed crystal of crystal form B and crystal form A.

The inorganic base is preferably selected from the group consisting of ammonia, sodium hydroxide, potassium hydroxide, sodium carbonate or potassium carbonate. When the palbociclib salt compound is a disalt, the amount of the inorganic base is preferably >2.0 equivalents, more preferably 2.2 to 3.0 equivalents. When the palbociclib salt compound is a single salt, the amount of the inorganic base is preferably >1.0 equivalents, more preferably 1.2 to 2.0 equivalents.

The water-miscible organic solvent is preferably selected from the group consisting of methanol, ethanol, isopropanol and tetrahydrofuran.

In a preferred embodiment, a volume ratio of water and the organic solvent in the aqueous solvent is preferably 1: (0-20), more preferably 1: (0-2).

The treatment is performed at a temperature of preferably 35-100° C., more preferably 50-70° C.

The treatment is performedat a pH of preferably >8.0, more preferably >10.0.

Another aspect of the present invention is to provide a method for preparing a crystal form B of palbociclib free base. The method comprises the following step: treating a palbociclib salt compound with an inorganic base in an aqueous solvent at a temperature of 0° C. to 20° C. to obtain a crystal form B of palbociclib free base, wherein the aqueous solvent is water or a mixed solvent of water and water-miscible organic solvent.

In a preferred embodiment, the method comprises following steps: dissolving palbociclib salt compound into an aqueous solvent to form a solution, and then treating the solution with an inorganic base water solution at a temperature of 0° C. to 20° C. to obtain a crystal form B of palbociclib free base, wherein the aqueous solvent is water or a mixed solvent of water and water-miscible organic solvent.

In the present invention, the palbociclib salt compounds are preferably selected from the group consisting of palbociclib isethionate, palbociclib hydrochloride, palbociclib sulfate, and palbociclib methane sulfonate or a combinations thereof, more preferably palbociclib isethionate and/or palbociclib hydrochloride.

The palbociclib salt compound can be in solid form or in solution form. It can be also a single salt, or a mixture of salts, or a mixture of salt and free base.

In a preferred embodiment of the present invention, the palbociclib salt compound can be formed by dissolving palbociclib free base and an acid into a solvent. The acid is selected from the group consisting of sulfuric acid, isethionic acid, methane sulfonic acid, hydrochloric acid or nitric acid.

The inorganic base is selected from the group consisting of ammonia, sodium hydroxide, potassium hydroxide, sodium carbonate or potassium carbonate. When the palbociclib salt compound is a disalt, the amount of the inorganic base is preferably >2.0 equivalents, more preferably 2.2 to 3.0 equivalents. When the palbociclib salt compound is a single salt, the amount of the inorganic base is preferably >1.0 equivalents, more preferably 1.2 to 2.0 equivalents.

The water-miscible organic solvent is at least one preferably selected from the group consisting of methanol, ethanol, isopropanol and tetrahydrofuran. In a preferred embodiment, a volume ratio of water and the organic solvent in the aqueous solvent is preferably 1:(0-20), more preferably 1:(0-2).

The treatment is performed at a temperature of preferably 0-20° C., more preferably 5-15° C.

The treatment is performed at a pH of preferably >8.0, more preferably >10.0.

The beneficial effects of the present invention are as follows. The inventors of the present invention have found that crystal form A and crystal form B of palbociclib free base can be obtained from an aqueous solvent. The preparation method provided by the present invention is performed under mild conditions, easy to control, and can be stably scaled up, is suitable for large-scale industrial production.

BRIEF DESCRIPTION OF THE DRAWINGS

In order to illustrate the examples of the present invention and the technical solutions of the prior arts more clearly, the drawings used in the examples and the prior art. are briefly described below. Obviously, the drawings in the following description are only some examples of the present invention, For those ordinary skilled in the art, other drawings can be also obtained according to these drawings without any creative work.

DETAILED DESCRIPTION OF THE INVENTION

Figure 1:
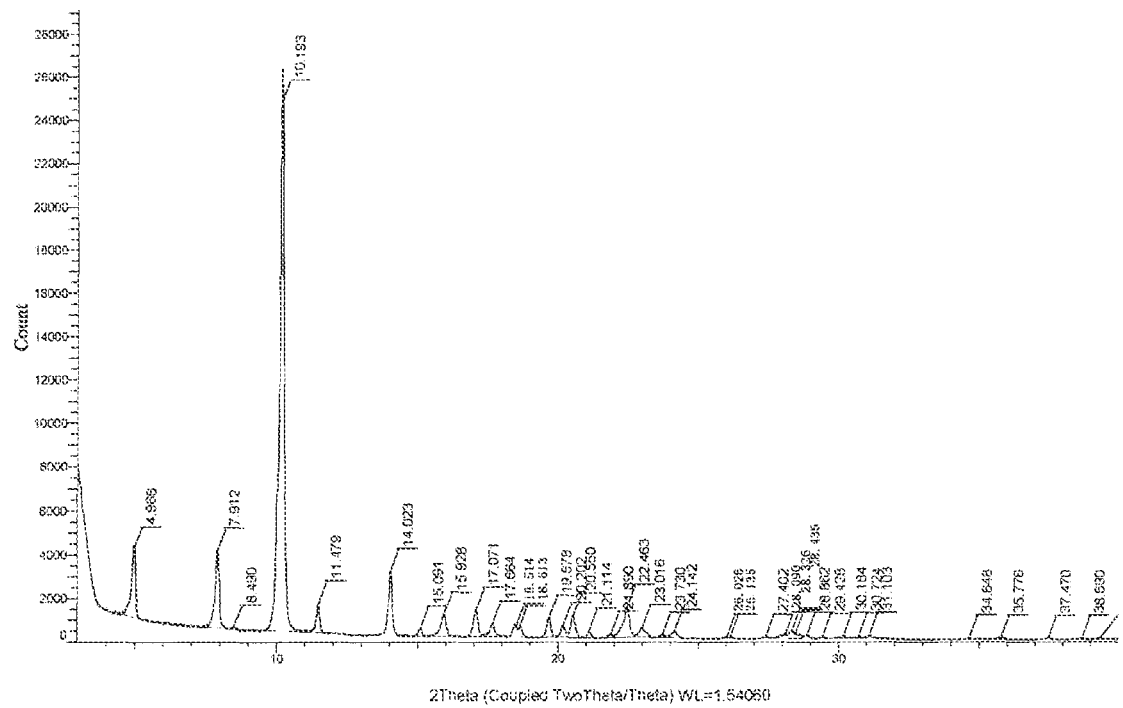
FIG. 1 shows an X-ray powder diffraction pattern of a crystal form A of palbociclib.
Figure 2:
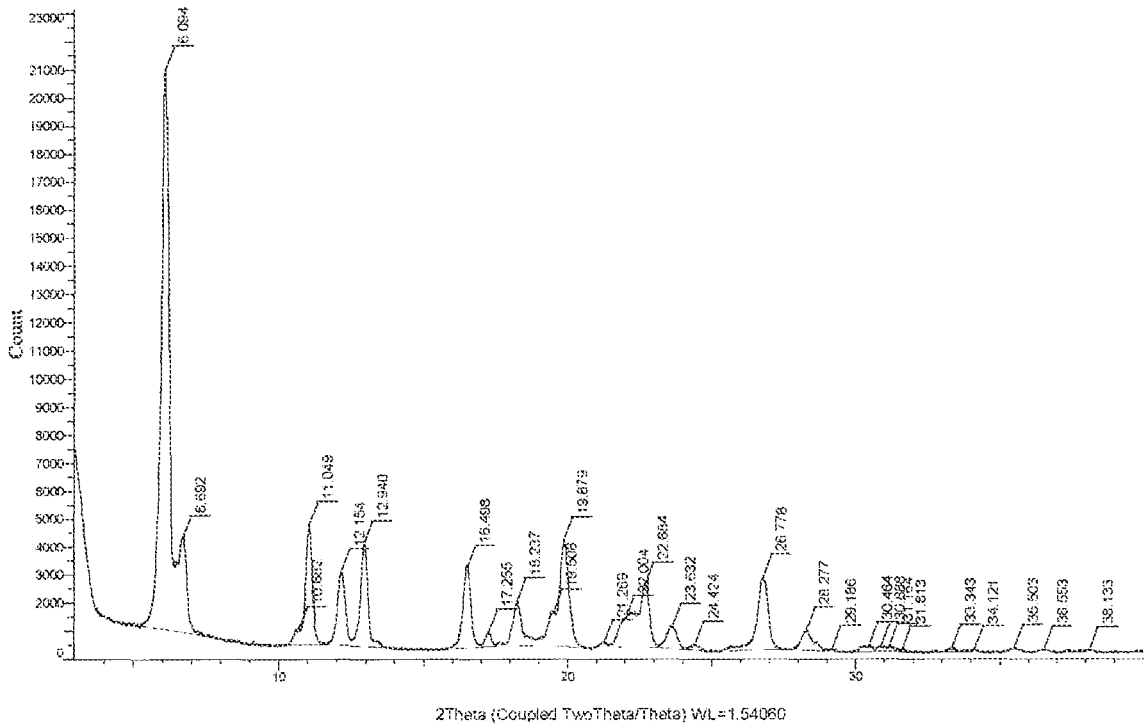
FIG. 2 shows an X-ray powder diffraction pattern of a crystal form B of palbociclib.

To illustrate the purposes, technical solutions and advantages of the present invention, the present invention will be further described in detail with the following accompanying drawings and examples. Obviously, the described examples are only a part of the examples of the present invention, rather than all of the examples. All other examples obtained by an ordinary skilled person in the art based on the examples of the present invention without creative efforts shall be within the scope of the present invention.

X-Ray Powder Diffraction (XRPD) Analysis Conditions: BRUKER D8 Advance Measurement (Luke Corporation) is used with specific voltage and current: 40 kV, 40 mA. Goniometer: vertical goniometer, radius 280 mm; slit: DS=2°, SS=½°, mask=15 mm, RS=5.0 mm; detector: LYNXEYE detector; scan mode: continuous scan; scan range: 3 to 40°; count time per step: 0.2 seconds; total scan time: 390 seconds.

EXAMPLE 1

Preparation of palbociclib isethionate: 1.00 g of tert-butyl 4-[6-[(6-(1-butoxyvinyl)-8-cyclopentyl-7,8-dihydro-5-methyl-7-oxopyridino [2,3-D]pyrimidin-2-yl)amino]-3-pyridyl]-1-piperazine carboxylate was added into a 2 L three-necked flask, and then 1.0 L methanol, 90.4 g isethionic acid and 50 ml water were added. The mixture was heated to 60-65° C. and stirred for 3-4 hours. The system was then cooled to 0-5° C., crystallized, and suction filtrated to obtain a yellow solid. The resulting solid was purified via recrystallization from a methanol/water mixed solvent, dried to obtain 94.5 g (yield: 81.5%) yellow fluffy solid, with HPLC purity of 99.8%

EXAMPLE 2

Preparation of palbociclib hydrochloride: 100 g tert-butyl 4-[6-[(6-(1-butoxyvinyl)-8-cyclopentyl-7,8-dihydro-5-methyl -7-oxopyridino [2,3-D]pyrimidin-2-yl)amino]-3-pyridyl]-1-piperazine carboxylate was added into a 2 L three-necked flask, and then 1.0 L methanol, 41.5 ml hydrochloric acid and 100 ml water were added. The mixture was heated to 60-65° C. and stirred for 3-4 hours. The system was then cooled to 0-5° C., crystallized, and suction filtrated to obtain a yellow solid. The resulting solid was purified via recrystallization from a methanol/water mixed solvent, dried to obtain 63.4 g (yield: 72.4%) yellow fluffy solid, with HPLC purity of 99.8%,

EXAMPLE 3

Preparation of palbociclib free base: 40.0 g palbociclib isethionate (prepared in example 1) was dissolved into 700 ml water to form palbociclib isethionate solution. 20.0 g sodium carbonate was dissolved into 320 ml water and stirred at 30° C., and then palbociclib isethionate solution was added dropwise into the solution of sodium carbonate with stirring, and a yellow solid was precipitated. After that, the mixture was stirred at a constant temperature of 30° C. for 1 hour. Suction filtration and drying was introduced. to obtain 0.97 g (yield: 97.0%) yellow solid, with HPLC purity of 99.8%.

EXAMPLE 4

Preparation of a crystal form A of palbociclib free base: 92.0 g palbociclib isethionate (prepared in example 1) was dissolved in 1.8 L water to form palbociclib isethionate solution. 13.1 g sodium hydroxide was dissolved into 1.8 L water and stirred at 50° C.-60° C., and then the palbociclib isethionate solution was added dropwise into the solution of sodium hydroxide with stirring, and a yellow solid was precipitated. After that (sample was taken and monitored by XRPD, a crystal form A had been formed), the mixture was stirred at a constant temperature of 50° C.-60° C. for 2 hours. Suction filtration and drying was introduced to obtain 55.7 g (yield: 94.7%) yellow solid, with HPLC purity of 99.8%. The product was analyzed by XRPD as the crystal form A.

EXAMPLE 5

Preparation of a crystal form A of palbociclib free base: 1.0 g palbociclib free base (prepared in example 3) and 0.7 g isethionic acid were dissolved into 24 ml mixed solvent of water and methanol to form a solution of palbociclib isethionate. 0.43 g sodium carbonate was dissolved in 32 ml water with stirring at 35° C., and the solution of the palbociclib isethionate was added dropwise into the solution of sodium carbonate with stirring, then a yellow solid was precipitated. After that (sample was taken and monitored by XRPD, crystal form A had been formed), the mixture was stirred at a constant temperature of 35° C. for 1 hour. Suction filtration and drying was introduced to give 0.97 g (yield: 97.0%) yellow solid, with HPLC purity of 99.8%. The product was analyzed by XRPD as the crystal form A.

EXAMPLE 6

Preparation of a crystal form A of palbociclib free base: 1.6 g palbociclib hydrochloride (prepared in example 2) was dissolved into 40 ml water to form palbociclib hydrochloride solution. 0.38g sodium hydroxide was dissolved in 30 ml water and stirred at 100° C., and the palbociclib hydrochloride solution was added dropwise into the solution of sodium hydroxide with stirring, then a yellow solid was precipitated. After that, suction filtration and drying was introduced to obtain 1.32 g (yield: 96%) yellow solid, with HPLC purity of 99.9%. The product was analyzed by XRPD as the crystal form A.

EXAMPLE 7

Preparation of a crystal form A of palbociclib free base: 1.0 g palbociclib free base (prepared in example 3) and 0.3 g sulfuric acid were dissolved into 25 ml mixed solvent of water and ethanol to form a solution of palbociclib sulfate. 0.51 g potassium carbonate was dissolved in 32 ml water with stirring at 40° C., and the solution of the palbociclib sulfate was added dropwise into the potassium carbonate solution with stirring, then a yellow solid was precipitated. After that, the mixture was stirred at a constant temperature of 40° C. for 1 hour. Suction filtration and drying was introduced to obtain 0.96 g (yield: 96.0%) yellow solid, with HPLC purity of 99.8%. The product was analyzed by XRPD as the crystal form A.

EXAMPLE 8

Preparation of a crystal form A of palbociclib free base: 1.0 g palbociclib free base (prepared in example 3) and 0.45 g methane sulfonic acid were dissolved into 25 ml mixed solvent of water and isopropyl alcohol to form a solution of palbociclib methanesulfonate. 0.21 g potassium hydroxide was dissolved in 30 ml water with stirring at 55° C., and the solution of the palbociclib methanesulfonate was added dropwise into the potassium hydroxide solution with stirring, then a yellow solid was precipitated. After that, suction filtration and drying was introduced to obtain 0.95 g (yield: 95.0%) yellow solid, with HPLC purity of 99.8%. The product was analyzed by XRPD as the crystal form A.

EXAMPLE 9

Preparation of a crystal form A of palbociclib free base: 8.0 g palbociclib isethionate (prepared in example 1), 2.0 g palbociclib hydrochloride (prepared in example 2) and 3 g palbociclib free base (prepared in example 3) were dissolved into 250 ml mixed solvent of water and tetrahydrofuran to form a mixed palbociclib solution. 10 g ammonia was dissolved in 150 ml water with stirring at 35° C., and the mixed palbociclib solution was added dropwise to the aqueous ammonia solution with stirring, then a yellow solid was precipitated. After that, the mixture was stirred at a constant temperature of 35° C. for 0.5 hour. Suction filtered and drying was introduced to obtain 9.1 g (yield: 92.4%) yellow solid, with HPLC purity of 99.8%. The product was analyzed by XRPD as the crystal form A.

EXAMPLE 10

Preparation of a crystal form B of palbociclib free base: 1.0 g palbociclib isethionate (prepared in example 1) was dissolved into 9 ml water to form a mixture, and the mixture was slowly added dropwise to a solution of 0.22 g sodium hydroxide and 32 ml water. The temperature was controlled at 20° C. and an orange-yellow solid was precipitated (the sample was taken and monitored by XRPD, crystal form B had been formed). The mixture was stirred at 20° C. overnight, then suction filtration, rinsing with water, and drying was introduced to obtain 0.60 g (yield: 93.9%) yellow solid. The product was analyzed by XRPD as the crystal form B.

EXAMPLE 11

Preparation of a crystal form B of palbociclib free base: 1.0 g palbociclib free base (prepared in example 3) and 0.7 g isethionic acid were dissolved into 24 ml mixed solvent of water and methanol to form a solution of palbociclib isethionate, 0.45 g sodium carbonate was dissolved in 40 ml water with stirring at 0° C., and the solution of palbociclib isethionate was added dropwise to the sodium carbonate solution with stirring, then a yellow solid was precipitated. The mixture was stirred at a constant temperature of 0° C. for 1 hour. Suction filtration and drying was introduced to obtain 0.97 g (yield: 97.0%) yellow solid, with HPLC purity of 99.8%. The product was analyzed by XRPD as the crystal form B.

EXAMPLE 12

Preparation of a crystal form B of palbociclib free base: A mixture of 130 g palbociclib isethionate (prepared in example 1) and 22.5 g palbociclib hydrochloride (prepared in example 2) was dissolved into 1.5 L water and transferred into a 5 L four-necked flask. 150 g ammonia water and 1.5 L water was mixed and added dropwise into the above mixture at 25° C. A large amount of solids precipitated. Stirring for 3 hours, suction filtration, rinsing with water and drying was introduced to obtain 96.1 g (yield: 93.6%) yellow solid, with HPLC purity of 99.9%. The product was analyzed by XRPD as the crystal form B.

EXAMPLE 13

Preparation of a crystal form B of palbociclib free base: 0.80 g palbociclib hydrochloride (prepared in example 2) and 0.3 g palbociclib free base (prepared in example 3) were dissolved into 25 ml mixed solvent of water and isopropyl alcohol to form a mixed palbociclib solution. 0.19 g sodium hydroxide was dissolved in 15 ml water with stirring at 10° C., and the mixed palbociclib solution was added dropwise into solution of sodium hydroxide with stirring, then a yellow solid was precipitated. After that, suction filtration and drying was introduced to obtain 0.85 g (yield: 85.8%) yellow solid, with HPLC purity of 99.9%. The product was analyzed by XRPD as the crystal form B.

EXAMPLE 14

Preparation of a crystal form B of palbociclib free base: 2.0 g palbociclib free base (prepared in example 3) and 0.7 g sulfuric acid were dissolved into 50 ml mixed solvent of water and ethanol to form a solution of palbociclib sulfate. 1.0 g potassium carbonate was dissolved in 35 ml water with stirring at 15° C., and the solution of palbociclib sulfate was added dropwise to the potassium carbonate solution with stirring, then a yellow solid was precipitated. After that, the mixture was stirred at a constant temperature of 15° C. for 1 hour. Suction filtration and drying was introduced to obtain 1.85 g (yield: 92.50%) yellow solid, with HPLC purity of 99.8%. The product was analyzed by XRPD as the crystal form B.

EXAMPLE 15

Preparation of a crystal form B of palbociclib free base: 1.0 g palbociclib free base (prepared in example 3) and 0.45 g methane sulfonic acid were dissolved into 25 ml mixed solvent of water and tetrahydrofuran (volume ratio of 1:0.15) to form a solution of palbociclib methanesulfonate. 0.25 g potassium hydroxide was dissolved in 30 ml water with stirring at 15° C., and the solution of palbociclib methanesulfonate was added dropwise to the potassium hydroxide solution with stirring, then a yellow solid was precipitated, After that, suction filtration and drying was introduced to obtain 0.94 g (yield: 94.0%) yellow solid, with HPLC purity of 99.8%. The product was analyzed by XRPD as the crystal form B.

EXAMPLE 16

Preparation of a crystal form A of palbociclib free base: 150 g palbociclib isethionate (prepared in example 1) was dissolved into 1.5l. water and transferred into a 5 L four-necked flask. 150 g ammonia water and 1.5 L water was mixed and added dropwise into the four-necked flask at 25° C. A large amount of solids were precipitated, stirred for 3 hours (the sample was taken and monitored by XRPD, crystal form B had been formed). The mixture was heated to 50° C.-60° C. and stirred for 4 hours, then suction filtration, rinsing with water and drying was introduced to obtain 89.3 g (yield: 93.2%) yellow solid, with HPLC purity of 99.9%. The product was analyzed by XRPD as the crystal form A.

EXAMPLE 17

Preparation of a crystal form A of palbociclib free base: 0.5 g sodium hydroxide was dissolved into 20 ml water and heated to 100° C. 1.0 g crystal form B (prepared in example 12) was added thereto and stirred for 1 hour. Suction filtration and drying was introduced to obtain 0.97g (yield: 97.0%) yellow solid, with HPLC purity of 99.8%. The product was analyzed by XRPD as the crystal form A.

EXAMPLE 18

Preparation of a crystal form A of palbociclib free base: 0.5 g sodium carbonate was dissolved into 20 ml mixed solvent of water and methanol (volume ratio 1:2) and heated to 50° C. 1.0 g crystal form B (prepared in example 12) was added thereto and stirred for 1 hour. Suction filtration and drying was introduced to obtain 0.98 g (yield: 98.0%) yellow solid, with HPLC purity of 99.9%. The product was analyzed by XRPD as the crystal form A.

EXAMPLE 19

Preparation of a crystal form A of palbociclib free base: 0.5 g potassium carbonate was dissolved into 30 ml mixed solvent of water and ethanol (volume ratio 1:1) and heated to 60° C. 1.0 g crystal form B (prepared in example 12) was added thereto and stirred for 1 hour. Suction filtration and drying was introduced to obtain 0.99 g (yield: 99.0%) yellow solid, with HPLC purity of 99.9%. The product was analyzed by XRPD as the crystal form A.

EXAMPLE 20

Preparation of a crystal form A of palbociclib free base: 5 g potassium hydroxide was dissolved into 300 ml mixed solvent of water and isopropyl alcohol (volume ratio 1:0.2) and heated to 35° C. 10.0 g crystal form B (prepared in example 12) was added thereto, and 0.2 g crystal form A (prepared in example 4) was added as seed crystal. The mixture was stirred for 3 hours. Suction filtration and drying was introduced to obtain 10.0 g (yield: 98.0%) yellow solid, with HPLC purity of 99.9%. The product was analyzed by XRPD as the crystal form A.

EXAMPLE 21

Preparation of a crystal form A of palbociclib free base: 5 g ammonia water was dissolved into 300 ml mixed solvent of water and tetrahydrofuran (volume ratio 1:0.1) and heated to 35° C. A mixture of 10.0 g crystal form B (prepared in example 12) and crystal form A (prepared in example 4) was added thereto and stirred for 3 hours. Suction filtration and drying was introduced to obtain 9.9 g (yield: 99.0%) yellow solid, with HPLC purity of 99.9%. The product was analyzed by XRPD as the crystal form A.

EXAMPLE 22

Characteristic peaks of a crystal form A of palbociclib free base: The X-ray powder diffraction pattern of a crystal form A of palbociclib free base (prepared in example 4) was detected by using Cu-Kα radiation. The 2θ angles and relative intensities of the characteristic peaks are shown in Table 1.

TABLE 1

Characteristic peaks of a crystal form A of palbociclib free base

| 2θ | relative intensities |
|---|---|
| 4.966 | 12.8% |
| 7.912 | 14.5% |
| 10.193 | 100% |
| 11.479 | 5.4% |
| 14.023 | 12.1% |

EXAMPLE 23

Characteristic peaks of a crystal form B of palbociclib free base: The X-ray powder diffraction pattern of a crystal form B of palbociclib free base (prepared in example 10) was detected by using Cu-Kα radiation. The 29 angles and relative intensities of the characteristic peaks are shown in Table 1.

TABLE 2

Characteristic peaks of palbociclib free base crystal form B

| 2θ | relative intensities |
|---|---|
| 6.094 | 100.0% |
| 6.692 | 16.7% |

TABLE 2-continued

Characteristic peaks of palbociclib free base crystal form B

| 2θ | relative intensities |
|---|---|
| 11.049 | 21.4% |
| 12.154 | 13.1% |
| 12.940 | 18.3% |
| 16.498 | 14.1% |
| 19.879 | 19.0% |
| 22.684 | 11.0% |
| 26.778 | 12.9% |

COMPARATIVE EXAMPLE 1

Preparation of a crystal form A of palbociclib free base: according to the method disclosed in WO2014128588A1, 1.0 eq. palbociclib free base in n-butanol (320 ml, 16 ml/g) and anisole (480 ml, 24 ml/g) was heated to 95-100° C. and remained insoluble. The seed crystal of crystal form A was required to be added into the reaction system to obtain a crystal form A of palbociclib free base.

COMPARATIVE EXAMPLE 2

Preparation of a crystal form B of palbociclib free base: according to the method disclosed in WO2014128588A1, in the case of adding seed crystal, stable crystal form B cannot be obtained.

It can be seen from the above examples and comparative examples that the preparation method of crystal form A and crystal form B of palbociclib free base provided according to the present invention can be performed in a solvent of water or a mixed solvent of water and water-miscible organic solvent to obtain crystal form A and crystal form B of palbociclib free base, with a high yield and a high purity under milder experimental conditions. The method provided by the present invention has the advantages of mild condition, easy to control, and stable scaling up. Stable crystal form A and crystal form B can be obtained, and solids in both crystal forms can realize industrial production.

The above are only the preferred examples of the present invention and are not intended to limit the present invention. Any modifications, equivalent substitutions and improvements made within the spirit and principle of the present invention should be included in the protection scope of the present invention.

The invention claimed is:

1. A method for preparing crystal form B of palbociclib of the Formula I: the method comprising:

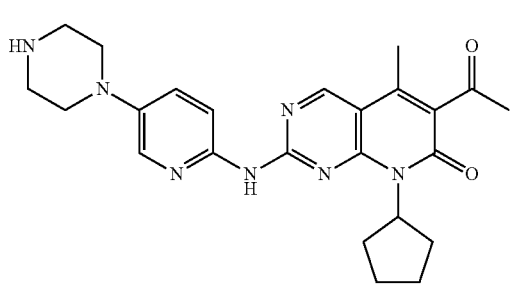

treating a pharmaceutically acceptable salt of palbociclib with a base selected from the group consisting of ammonia, sodium hydroxide, potassium hydroxide, sodium carbonate and potassium carbonate in an aqueous solvent selected from the group consisting of water and a co-solvent mixture consisting of water and a water-miscible organic solvent selected from the group consisting of methanol, ethanol, isopropanol and tetrahydrofuran, at a temperature in the range of 0° C. to 20° C., to obtain crystal form B of palbociclib;

wherein crystal form B of palbociclib exhibits an X-ray powder diffraction pattern comprising characteristic peaks having 2θ angles selected from the group consisting of 6.094°, 6.692°, 11.049°, 12.154°, 12.940°, 16.498°, 19.879°, 22.684°, and 26.778°.

2. The method according to claim 1, wherein the pharmaceutically acceptable salt of palbociclib is selected from the group consisting of palbociclib isethionate, palbocklib hydrochloride, palbociclib sulfate, and palbociclib methane sulfonate or a combination thereof.

3. The method according to claim 1, wherein the inorganic base is selected from the group consisting of sodium hydroxide, potassium hydroxide, sodium carbonate, and potassium carbonate.

4. The method according to claim 1, wherein the water-miscible organic solvent is selected from the group consisting of methanol, ethanol and isopropanol.

5. The method according to claim 1, wherein the volume ratio of water and the water-miscible organic solvent in the aqueous solvent is 1:0 to 1:20.

6. The method according to claim 1, wherein the volume ratio of water and the water-miscible organic solvent in the aqueous solvent is 1:0 to 1:2.

7. The method according to claim 1, wherein the treatment is performed at a pH greater than 8.0.

8. The method according to claim 1, wherein the treatment is performed at a pH greater than 10.0.

9. The method according to claim 1, wherein the treatment is performed at a temperature in the range of 5 ° C. to 15 ° C.

* * * * *

UNITED STATES PATENT AND TRADEMARK OFFICE
CERTIFICATE OF CORRECTION

PATENT NO. : 10,766,895 B2
APPLICATION NO. : 16/405722
DATED : September 8, 2020
INVENTOR(S) : Haisheng Fan et al.

Page 1 of 1

It is certified that error appears in the above-identified patent and that said Letters Patent is hereby corrected as shown below:

On the Title Page

Item (62) Related U.S. Application Data should read:
--Division of application No. 15/772,497, filed as application No. PCT/CN2016/104330 on Nov. 2, 2016, now Pat. No. 10,329,290.--

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*